United States Patent [19]

McClanahan

[11] Patent Number: 4,990,328

[45] Date of Patent: Feb. 5, 1991

[54] ANTICALCULUS COMPOSITIONS

[75] Inventor: Stephen F. McClanahan, Loveland, Ohio

[73] Assignee: The Procter & Gamble Company, Cincinnati, Ohio

[21] Appl. No.: 321,249

[22] Filed: Mar. 9, 1989

[51] Int. Cl.$^5$ .......................... A61K 9/16; A61K 9/18
[52] U.S. Cl. .......................................... 424/52; 424/49; 424/57
[58] Field of Search ...................................... 424/49-58

[56] References Cited

U.S. PATENT DOCUMENTS

| | | | |
|---|---|---|---|
| 4,515,772 | 5/1985 | Parran et al. | 424/57 |
| 4,518,430 | 5/1985 | Brown et al. | 106/35 |
| 4,753,652 | 6/1988 | Langer et al. | 623/1 |

OTHER PUBLICATIONS

Howard, J. E., "Studies on Urinary Stone Formation a Saga of Clinical Investigation", *Johns Hopkins Medical Journal*, 139 (6), 1976, pp. 239-252.

Gimenez et al., "Phosphocitrate Prevents Phosphate Induced Loss of Renal Function in Experimental Aremia", *Clinical Research*, 29 (2), 1981, p. 539A.

Tew et al., "The Effects of Phosphocitrate on Experimentally Induced Nephro Calcinosis", *Kidney International*, 19 (1) 1981, p. 117.

*Primary Examiner*—Shep K. Rose
*Attorney, Agent, or Firm*—Douglas C. Mohl; Kim William Zerby; Jack D. Schaeffer

[57] ABSTRACT

Disclosed are oral compositions containing phosphocitrate to provide improved anticalculus activity.

9 Claims, No Drawings

ANTICALCULUS COMPOSITIONS

TECHNICAL FIELD

The present invention relates to oral compositions containing phosphocitrate which provide an improved anticalculus benefit.

BACKGROUND OF THE INVENTION

Dental calculus, or tartar as it is sometimes called, is a deposit which forms on the surfaces of the teeth of humans and some lower animals at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars.

Mature calculus consists of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris and various types of microorganisms.

As the mature calculus develops, it becomes visibly white or yellowish in color unless stained or discolored by some extraneous agent. This is undesirable from an aesthetic standpoint.

A wide variety of chemical and biological agents have been suggested in the art to retard calculus formation or to remove calculus after it is formed. Mechanical removal of this material periodically by the dentist is, of course, routine dental office procedure.

The chemical approach to calculus inhibition generally involves chelation of calcium ion and/or crystal growth inhibition which prevents the calculus from forming and/or breaks down mature calculus by removing calcium.

The prior art discloses a number of chelating agents for this purpose. British Patent No. 490,384, Feb. 15, 1937, discloses oral compositions containing ethylenediaminetetraacetic acid, nitrilotriacetic acid and related compounds as anticalculus agents. U.S. Pat. No. 3,678,154, Jul. 18, 1972 to Widder et al. discloses oral compositions containing certain polyphosphonates and fluoride. U.S. Pat. No. 3,737,533, Jun. 5, 1973 to Francis discloses oral compositions containing certain carbonyl diphosphonates.

In addition to the above references, the prior art discloses dentifrices and mouthwashes containing soluble pyrophosphate salts which have been included for a variety of purposes but not all for anticalculus purposes. Included among such references are U.S. Pat. No. 2,941,926, Jun. 21, 1960 to Salzmann et al. which discloses dental powders containing chlorophyll and pyrophosphate salts. U.S. Pat. No. 3,137,632, Jun. 16, 1964 to Schiraldi discloses toothpastes containing pyrophosphate salts. U.S. Pat. Nos. 3,927,201 and 202, Dec. 16, 1975 to Baines et al. and Harvey et al., respectively, disclose toothpastes which utilize soluble pyrophosphates as abrasives. U.S. Pat. Nos. 4,244,931, Jan. 13, 1981 and 4,247,526, Jan. 27, 1981 to Jarvis et al. disclose pyrophosphate salts in dicalcium phosphate systems. Jap. Patent Application Disclosure No. 4945-1974 discloses soluble pyrophosphates in a variety of dentifrice systems. U.S. Pat. No. 4,333,551, Apr. 6, 1982 to Parran discloses tetraalkali metal salts in mouthwash compositions. U.S. Pat. No. 4,515,772, May 7, 1985 to Parran, et al., discloses composition containing soluble pyrophosphate salts as anticalculus agents. U.S. Pat. No. 4,627,977, Dec. 9, 1986 to Gaffar et al., discloses oral compositions containing mixtures of polyphosphates and linear, anionic polymers as anticalculus agents.

In addition to the use of the above mentioned materials the use of certain acrylic acid polymers and other agents have also been disclosed for use as anticalculus agents. Included among such agents are polyelectrolytes such as copolymers of maleic anhydride and ethylene disclosed in U.S. Pat. No. 3,429,963, Feb. 25, 1969 to Shedlovsky. Shedlovsky also discloses polyacrylic acid having an average molecular weight of 1500 and greater. Another reference disclosing polyacrylic acids in oral compositions is South African Patent No. 720,898, Sept. 12, 1972 which discloses such acids having a molecular weight in the range of 2,000 to 4,000,000 for use as a membrane to prevent the elution from teeth of previously applied agents. U.S. Pat. No. 3,956,480, May 11, 1976 to Gaffar discloses complexes of anionic polymers (e.g. acrylic acid) and a cationic therapeutic agent (e.g., chlorhexidine) as anticalculus agents. Strontium chelates have also been disclosed for use in oral compositions, particularly in the enhancement of fluoride uptake.

Phosphocitrate has been widely disclosed in the medical literature for a variety of purposes. One very widely reported use is for the prevention of stone formation in the kidneys or urinary tract. Among references disclosing this use are Howard, J. E., "Studies on Urinary Stone Formation a Saga of Clinical Investigation", *Johns Hopkins Medical Journal* 139 (6), 1976, pages 239-252; Gimenez, et al., "Phosphocitrate Prevents Phosphate Induced Loss of Renal Function in Experimental Aremia", *Clinical Research*, 29 (2), 1981, page 539A; and Tew et al., "The Effects of Phosphocitrate on Experimentally Induced Nephro Calcinosis", *Kidney International* 19 (1) 1981, page 117.

Another area where phosphocitrate has been disclosed to have utility is in the area of prevention of hydroxyapatite formation in bone and cartilage. A reference disclosing this use is Reddi et al., "Influence of Phosphocitrate, a Potent Inhibition of Hydroxylapatite Crystal Growth, on Mineralization of Cartilage and Bone", *Biochem. Biophys. Res. Commun.*, 97 (1), pages 154–159.

Although there have been a number of approaches disclosed for combatting calculus, there is still the desire and need to develop additional products possessing that property. The prior art while disclosing the use of phosphocitrate for a variety of purposes does not suggest its use for reducing calculus through the topical application to dental enamel in the mouths of humans or lower animals.

It is an object of the present invention to provide compositions which deliver an anticalculus benefit.

It is a further object of the present invention to produce an effective anticalculus product using a phosphocitrate material.

It is still a further object of the present invention to provide anticalculus products which are cosmetically acceptable and do not inhibit remineralization of the teeth.

It is still a further object of the present invention to provide effective methods for combating calculus.

These and other objects will become more clear from the detailed description which follows.

All percentages and ratios used herein are by weight and all measurements are made at 25° C. unless otherwise specified.

SUMMARY OF THE INVENTION

The present invention embraces an oral composition comprising:
(a) a safe and effective amount of a phosphocitrate material; and
(b) an acceptable carrier.

The present invention also encompasses a method for retarding development of dental calculus with the above compositions.

DETAILED DESCRIPTION OF THE INVENTION

The compositions of the present invention comprise phosphocitrate in an acceptable carrier.

By "oral compositions" as used herein means a product which in the ordinary course of usage is not intended for purposes of systemic administration of particular therapeutic agents, but is rather retained in the oral cavity for a time sufficient to contact substantially all of the dental surfaces and/or oral tissues for purposes of oral activity.

By "safe and effective amount" as used herein means sufficient amount of material to provide the desired benefit while being safe to the hard and soft tissues of the oral cavity.

By the term "comprising", as used herein, is meant that various additional components can be conjointly employed in the compositions of this invention as long as the listed materials perform their intended functions.

By the term "acceptable carrier", as used herein, is meant a suitable vehicle which can be used to apply the present anticalculus agents in the oral cavity.

Phosphocitrate Material

The anticalculus active used in the present invention is a "phosphocitrate" material. "Phosphocitrate" is an accepted name and the free acid has the following structure:

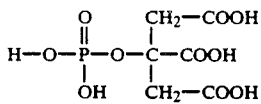

This material is found in trace amounts in certain human body fluids and can be prepared using the method described hereinafter. It is to be appreciated that the term "phosphocitrate material" includes the free acid, water soluble salts of the free acid such as the $NH_4^+$, $Na^+$, $K^+$, $Li^+$ etc. salts wherein the counterion is the same or different on the three carboxyl groups and phosphate group, carboxyl esters of phosphocitrate such as the mono-, di- or triethylester, and esters other than ethyl such as methyl, butyl etc. as well as similar esters on the phosphate group. Mixtures of these various forms may also be used.

The phosphocitrate material, as the anion form, is used at a level of from about 0.1% to about 10%, preferably from about 0.5 to about 7, most preferably from about 1 to about 5 of the total composition.

Acceptable Carrier

The carrier for the active ingredients herein can be any vehicle suitable for use in the oral cavity. Such carriers include the usual components of mouthwashes, dentifrices (e.g., toothpastes, toothpowders, prophylaxis pastes), lozenges, gums and the like and are more fully described hereinafter. Dentifrices and mouthwashes are the preferred systems.

The abrasive polishing material contemplated for use in the dentifrice compositions of the present invention can be any material which does not excessively abrade dentin. These include, for example, silicas including gels and precipitates, calcium pyrophosphate, calcium polymetaphosphate, insoluble sodium polymetaphosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride and other active, therapeutic agents. For these reasons they are preferred for use herein.

The silica abrasive polishing materials useful herein, as well as the other abrasives, generally have an average particle size ranging between about 0.1 and 30 microns, preferably 5 and 15 microns. The silica abrasive, as noted above, can be precipitated silica or silica gels such as the silica xerogels described in Pader et al., U.S. Pat. No. 3,538,230, issued Mar. 2, 1970 and DiGiulio, U.S. Pat. No. 3,862,307, Jun. 21, 1975, both incorporated herein by reference. Preferred are the silica xerogels marketed under the tradename "Syloid" by the W. R. Grace & Company, Davison Chemical Division. Preferred precipitated silica materials include those marketed by the J. M. Huber Corporation under the tradename, "Zeodent", particularly the silica carrying the designation "Zeodent 119". These silica abrasives are described in U.S. Pat. No. 4,340,583, Jul. 29, 1982, incorporated herein by reference.

The abrasive in the compositions described herein is present at a level of from about 6% to 70%, preferably from about 15% to about 25% when the dentifrice is a toothpaste. Higher levels, as high as 90%, may be used if the composition is a toothpowder.

Flavoring agents can also be added to dentifrice compositions. Suitable flavoring agents include oil of wintergreen, oil of peppermint, oil of spearmint, oil of sassafras, and oil of clove. Sweetening agents which can be used include aspartame, acesulfame, saccharin, dextrose, levulose and sodium cyclamate. Flavoring and sweetening agents are generally used in dentifrices at levels of from about 0.005% to about 2% by weight.

Dentifrice compositions can also contain emulsifying agents. Suitable emulsifying agents are those which are reasonably stable and foam throughout a wide pH range, including non-soap anionic, nonionic, cationic, zwitterionic and amphoteric organic synthetic detergents. Many of these suitable surfactants are disclosed by Gieske et al. in U.S. Pat. No. 4,051,234, Sept. 27, 1977, incorporated herein by reference.

It is common to have a water-soluble fluoride compound present in dentifrices in an amount sufficient to give a fluoride ion concentration of from about 0.0025% to about 5.0% by weight, preferably from about 0.005% to about 2.0% by weight, to provide anticaries effectiveness. Preferred fluorides are amine fluorides, sodium fluoride, stannous fluoride, indium fluoride, and sodium monofluorophosphate. Norris et al., U.S. Pat. No. 2,946,735, issued Jul. 26, 1960 and Widder et al., U.S. Pat. No. 3,678,154, issued Jul. 18, 1972 disclose such salts as well as others. Both patents are incorporated herein by reference.

Other materials useful in the present toothpastes include additional anticalculus agents which are known to provide calculus reduction. Many of such agents are disclosed in the references listed in the background section herein all of which are incorporated herein by reference. Preferred agents include soluble pyrophosphate salts, soluble polycarboxylic salts (e.g., polyacrylic acid), polyphosphates, polyphosphonates such as ethane hydroxy diphosphonate among many others. The pyrophosphate salts include alkali metal salts such as sodium potassium lithium and ammonium. Such salts are disclosed in U.S. Pat. No. 4,515,772, May 7, 1985 to Parran, et al., incorporated herein by reference. The additional agent(s) may be present at a level of from about 0.01% to about 10%, preferably from about 1% to about 5%.

Another agent useful in the present compositions is a metal ion which may provide additional anticalculus activity. Suitable metals include magnesium, zinc, copper, aluminum, iron and many others. These metals may be provided to the compositions as a water soluble salt (e.g., chloride) or chelated with a suitable chelating agent such as ethylene diamine tetracetic acid or phosphocitrate itself as well as others such as those disclosed in Japanese Laid Open Application No. 61-36211. Feb. 20, 1986 to Kito et al., incorporated herein by reference. Another reference disclosing suitable chelates is European Application 0265186. Apr. 27, 1988 to White, incorporated herein by reference.

Water is also present in the toothpastes of this invention. Water employed in the preparation of commercially suitable toothpastes should preferably be deionized and free of organic impurities. Water generally comprises from about 10% to 50%, preferably from about 20% to 40%, by weight of the toothpaste compositions herein. These amounts of water include the free water which is added plus that which is introduced with other materials such as with sorbitol.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents in an amount from 0.2% to 5.0% by weight of the total composition can be used.

It is also desirable to include some humectant material in a toothpaste to keep it from hardening. Suitable humectants include glycerin, sorbitol, and other edible polyhydric alcohols at a level of from about 15% to about 70%.

Another preferred embodiment of the present invention is a mouthwash composition. Conventional mouthwash composition components can also comprise the carrier for the agents of the present invention. Mouthwashes generally comprise from about 20:1 to about 2:1 of a water/ethyl alcohol solution and preferably other ingredients such as flavor, sweeteners, humectants and sudsing agents such as those mentioned above for dentifrices. The humectants, such as glycerin and sorbitol give a moist feel to the mouth. Generally, on a weight basis the mouthwashes of the invention comprise 5% to 60% (preferably 5% to 20%) ethyl alcohol, 0% to 20% (preferably 5% to 20%) of a humectant, 0% to 2% (preferably 0.01% to 1.0%) emulsifying agents, 0% to 0.5% (preferably 0.005% to 0.06%) sweetening agent such as saccharin, 0% to 0.3% (preferably 0.03% to 0.3%) flavoring agent, and the balance water. Other optional components described herein earlier for use in dentifrice products are also useful in the mouthwash compositions.

Suitable lozenge and chewing gum components are disclosed in U.S. Pat. No. 4,083,955, Apr. 11, 1978 to Grabenstetter et al., incorporated herein by reference.

The pH of the present compositions and/or its pH in the mouth can be any pH which is safe for the mouth's hard and soft tissues. Such pH's are generally from about 5 to about 9, preferably from about 6 to about 8.

METHOD OF MANUFACTURE

The compositions of the present invention can be made using processes conventionally used for making oral compositions.

A method of manufacturing phosphocitrate is set forth in "Synthesis and Characterization of Phosphocitric Acid, a Potent Inhibitor of Hydroxylapatite Crystal Growth" by W. P. Tew, C. Mahle, J. Benavides, J. E. Howard and A. L. Lehninger in *Biochemistry* 1980, Vol. 19, pp. 1983-1988, incorporated herein by reference.

COMPOSITION USE

The present compositions are used in a conventional manner wherein the amounts of product are what users generally use for the specific product execution in question.

The following examples further describe and demonstrate preferred embodiments within the scope of the present invention. The examples are given solely for illustration and are not to be construed as limitations of this invention as many variations thereof are possible without departing from the spirit and scope thereof.

EXAMPLE I

The following is a dentifrice composition representative of the present invention:

| Component | Wt. % |
| --- | --- |
| Water | 23.92 |
| Sorbitol | 35.00 |
| PEG-6 | 5.00 |
| Tetrasodium Phosphocitrate | 4.03 |
| Hydrated Silica | 24.00 |
| Flavor | 0.90 |
| Sodium Fluoride | 0.24 |
| Saccharin | 0.28 |
| Sodium Alkyl Sulfate (28% aqueous solution) | 5.00 |
| Titanium Dioxide | 0.53 |
| Xanthan Gum | 0.80 |
| Carboxyvinyl Polymer | 0.25 |
| Dye | 0.05 |
| Total | 100.00 |

EXAMPLE II

The following is another example of the present invention:

| Component | Wt. % |
| --- | --- |
| Water | 25.70 |
| Sorbitol | 32.00 |
| PEG-6 | 1.00 |
| Glycerin | 8.00 |
| Tetrasodium Phosphocitrate | 1.34 |
| Tetrasodium Pyrophosphate | 2.17 |
| Sodium Acid Pyrophosphate | 0.74 |
| Hydrated Silica | 22.00 |
| Flavor | 1.04 |
| Sodium Fluoride | 0.24 |
| Saccharin | 0.29 |
| Sodium Alkyl Sulfate (28% aqueous solution) | 4.00 |
| Titanium Dioxide | 0.53 |
| Carrageenan | 0.55 |
| Carboxyvinyl Polymer | 0.35 |
| Dye | 0.05 |
| Total | 100.00 |

EXAMPLE III

The following is an example of the present invention which contains three anticalculus agents:

| Component | Wt. % |
| --- | --- |
| Water | 24.37 |
| Sorbitol | 32.00 |
| Glycerin | 6.00 |
| PEG-6 | 3.00 |
| Tetrasodium Phosphocitrate | 1.34 |
| Disodium Ethanehydroxy Diphosphonate | 1.23 |
| Tetrasodium Pyrophosphate | 2.17 |
| Sodium Acid Pyrophosphate | 0.74 |
| Hydrated Silica | 22.00 |
| Flavor | 1.10 |
| Sodium Fluoride | 0.24 |
| Saccharin | 0.46 |
| Sodium Alkyl Sulfate (28% aqueous solution) | 4.00 |
| Titanium Dioxide | 0.50 |
| Xanthan Gum | 0.60 |
| Carboxyvinyl Polymer | 0.20 |
| Dye | 0.05 |
| Total | 100.00 |

EXAMPLE IV

The following is another example of the present invention:

| Component | Wt. % |
| --- | --- |
| Water | 26.14 |
| Sorbitol | 35.00 |
| PEG-6 | 5.00 |
| Tetrasodium Phosphocitrate | 3.36 |
| Hydrated Silica | 22.00 |
| Flavor | 1.00 |
| Sodium Fluoride | 0.24 |
| Saccharin | 0.28 |
| Sodium Alkyl Sulfate (28% aqueous solution) | 5.00 |
| Titanium Dioxide | 0.53 |
| Xanthan Gum | 0.55 |
| Carboxyvinyl Polymer | 0.35 |
| Zinc Chloride | 0.50 |
| Dye | 0.05 |
| Total | 100.00 |

EXAMPLE V

The following is another example of the present invention:

| Component | Wt. % |
| --- | --- |
| Water | 26.26 |
| Sorbitol | 32.00 |
| PEG-6 | 3.00 |
| Glycerin | 6.00 |
| Tetrasodium Phosphocitrate | 2.69 |
| Hydrated Silica | 22.00 |
| Flavor | 1.00 |
| Sodium fluoride | 0.24 |
| Saccharin | 0.46 |
| Sodium Alkyl Sulfate (28% aqueous solution) | 4.00 |
| Titanium Dioxide | 0.50 |
| Xanthan Gum | 0.60 |
| Polyacrylic Acid (Mass Average Molecular Weight 4500) | 1.00 |
| Dye | 0.05 |
| Total | 100.00 |

In the above examples similarly effective anticalculus compositions are obtained by using other levels of phosphocitrate within the range of 0.1% to 10% and other additional anticalculus agents such as a copolymer of vinyl methyl ether and maleic anhydride or metal ions such as magnesium.

What is claimed is:

1. An oral composition comprising:
   (a) a safe and effective amount of a phosphocitrate material; and
   (b) an acceptable mouthwash carrier for topical application in the mouth.

2. A composition according to claim 1 wherein the phosphocitrate material is selected from the group consisting of phosphocitrate, water soluble salts of phosphocitrate, short chain esters of phosphocitrate and mixtures thereof.

3. A composition according to claim 2 wherein the phosphocitrate material is selected from the group consisting of phosphocitrate, water soluble salts of phosphocitrate and mixtures thereof.

4. A composition according to claim 3 which in addition contains a soluble fluoride ion source.

5. A composition according to claim 4 which in addition contains a nonphosphocitrate anticalculus agent.

6. A composition according to claim 1 wherein the additional anticalculus agent is selected from the group consisting of metal ions, soluble pyrophosphate salts, polycarboxylic acids, polyphosphonates and mixtures thereof.

7. A composition according to claim 4 which is in the form of a mouthwash.

8. A method of reducing calculus by contacting the dental enamel surfaces in the mouth of a human or lower animal having the propensity to form calculus with a safe and effective amount of a composition according to claim 1.

9. A method according to claim 8 wherein said composition contains one or more additional anticalculus agents.

* * * * *